US012661504B2

(12) United States Patent
Eom

(10) Patent No.: US 12,661,504 B2
(45) Date of Patent: Jun. 23, 2026

(54) HIGH-FREQUENCY SKIN CARE DEVICE

(71) Applicant: Four S Tech Co., Ltd., Bucheon-si (KR)

(72) Inventor: Tae Min Eom, Seongnam-si (KR)

(73) Assignee: Four S Tech Co. , Ltd., Bucheon-si (KR)

( * ) Notice: Subject to any disclaimer, the term of this patent is extended or adjusted under 35 U.S.C. 154(b) by 296 days.

(21) Appl. No.: 18/498,044

(22) Filed: Oct. 31, 2023

(65) Prior Publication Data

US 2025/0050101 A1 Feb. 13, 2025

(30) Foreign Application Priority Data

Aug. 9, 2023 (KR) ........................ 10-2023-0104228

(51) Int. Cl.
| | |
|---|---|
| *A61F 7/00* | (2006.01) |
| *A61N 1/04* | (2006.01) |
| *A61N 1/05* | (2006.01) |
| *A61N 1/06* | (2006.01) |
| *A61N 1/32* | (2006.01) |
| *A61N 1/40* | (2006.01) |
| A61B 18/00 | (2006.01) |
| A61B 18/14 | (2006.01) |

(52) U.S. Cl.
CPC ........... *A61N 1/328* (2013.01); *A61N 1/0502* (2013.01); *A61N 1/06* (2013.01); *A61N 1/403* (2013.01); *A61B 2018/00196* (2013.01); *A61B 2018/143* (2013.01); *A61F 2007/0052* (2013.01); *A61F 2007/0088* (2013.01)

(58) Field of Classification Search
CPC .......... A61N 1/328; A61N 1/403; A61N 1/06; A61N 2/02; A61F 2007/0052; A61F 2007/0088; A61B 2018/00452–0047; A61B 2018/143
See application file for complete search history.

(56) References Cited

U.S. PATENT DOCUMENTS

| | | | |
|---|---|---|---|
| 2010/0249770 A1 | 9/2010 | Lee et al. | |
| 2018/0153618 A1* | 6/2018 | Chen ...................... | A61B 34/10 |
| 2020/0360072 A1* | 11/2020 | Kuang ................... | A61B 18/10 |

FOREIGN PATENT DOCUMENTS

| | | |
|---|---|---|
| JP | 2021-530336 A | 11/2021 |
| KR | 2005-0080004 A | 8/2005 |

(Continued)

OTHER PUBLICATIONS

Extended European search report (EESR) issued on May 6, 2024 in European Patent Application No. 23206883.3.

*Primary Examiner* — Jaymi E Della
(74) *Attorney, Agent, or Firm* — AJU IP Global PLLC

(57) ABSTRACT

Disclosed is a high-frequency skin care device. The high-frequency skin care device according to one aspect of the present disclosure includes a high-frequency generator configured to receive power and output a high-frequency current, a coil part configured to convert the high-frequency current output from the high-frequency generator into an alternating magnetic field, a needle assembly including a plurality of needles configured to be heated by the alternating magnetic field and come in contact with the skin to treat the skin, a mover configured to move the needle assembly and allow the needle assembly to be inserted into the skin, and a controller configured to control the high-frequency generator and the mover.

10 Claims, 7 Drawing Sheets

(56)　　　　　References Cited

FOREIGN PATENT DOCUMENTS

| | | | |
|---|---|---|---|
| KR | 10-1124675 B1 | 3/2012 | |
| KR | 10-2013-0009512 A | 1/2013 | |
| KR | 102133999 B1 * | 7/2020 | .......... A61B 18/082 |
| KR | 2021-0020664 A | 2/2021 | |

\* cited by examiner

155

155a

155b

EPIDERMIS

DERMIS

A

SUBCUTANEOUS
TISSUE

155

HIGH-FREQUENCY SKIN CARE DEVICE

CROSS-REFERENCE TO RELATED APPLICATION

This application claims priority to and the benefit of Korean Patent Application No. 10-2023-0104228, filed on Aug. 9, 2023, the disclosure of which is incorporated herein by reference in its entirety.

BACKGROUND

1. Field of the Invention

The present disclosure relates to a high-frequency skin care device, and more particularly, to a high-frequency skin care device that can prevent skin burns after skin treatment using high-frequency waves.

2. Discussion of Related Art

Human skin is made up of the epidermis, dermis, and subcutaneous fat. The epidermis prevents the entry of pathogens or the like and blocks the loss of body fluids, and the dermis contains fibrous proteins and matrix proteins such as collagen and elastin and serves to provide nutrition to the epidermis. Also, the subcutaneous fat is located under the dermis and serves to absorb pressure or impact from the outside and maintain body temperature.

As the skin ages, skin elasticity gradually decreases, and wrinkles are formed which are generally due to a decrease in the amount of matrix proteins such as collagen and elastin in the dermis and a decrease in the amount of moisture.

In order to improve fine lines, pores, aging, scars, and the like of the skin, a high-frequency skin care method is used in which an electrode configured to transmit electrical energy is inserted into the dermis to directly apply high-frequency energy to the dermis. High-frequency skin care technology is a method in which electrical energy having a frequency is directly applied to the human body using a fine needle as an electrode, wherein the electrical energy is converted into thermal energy at a site where the needle and the skin come in contact, and the converted thermal energy stimulates the regeneration of collagen and elastin which are skin growth factors.

However, in the conventional high-frequency skin care method, since heat is generated at the needle used as the electrode, heat is generated on the skin around the needle, and there is a problem that side effects such as skin reddening, a mild skin burn, or the like may occur at a treatment site after the treatment.

The related art of the present disclosure is disclosed in "Skin treatment device using high-frequency waves" of Korean Patent Registration No. 10-1124675 (Date of Publication: Mar. 19, 2012).

SUMMARY OF THE INVENTION

The present disclosure is directed to providing a high-frequency skin care device that can prevent skin burns after skin treatment using high-frequency waves.

Objectives of the present disclosure are not limited to the above-mentioned objective(s), and other unmentioned objective(s) should be clearly understood by those of ordinary skill in the art from the description below.

One aspect of the present disclosure provides a high-frequency skin care device including: a high-frequency generator configured to receive power and output a high-frequency current; a coil part configured to convert the high-frequency current output from the high-frequency generator into an alternating magnetic field; a needle assembly including a plurality of needles configured to be heated by the alternating magnetic field and come in contact with the skin to treat the skin; a mover configured to move the needle assembly and allow the needle assembly to be inserted into the skin; and a controller configured to control the high-frequency generator and the mover.

In the present disclosure, the coil part may include a substrate, a coil disposed on the substrate, and a plurality of through-holes formed between portions of the coil and through which the plurality of needles pass.

In the present disclosure, the substrate may be formed as a nonconductor and have one surface formed as a close contact surface configured to come in contact with the skin of a user during treatment and the other surface disposed on the coil.

In the present disclosure, the plurality of through-holes may be spaced apart at predetermined intervals and formed in a lattice shape.

In the present disclosure, the coil part may be disposed at a front end portion of a handpiece case.

In the present disclosure, each of the plurality of needles may include a circular rod part which is made of a nonconductor and has an upper end portion connected to the mover and a heat generator which is connected to the circular rod part and configured to generate heat due to the alternating magnetic field generated by the coil part.

In the present disclosure, the heat generator may be made of a conductor and convert the current flowing therein into heat by eddy current loss and hysteresis loss due to the alternating magnetic field.

In the present disclosure, the heat generated by the heat generator may be, without being transferred to the circular rod part, transmitted as thermal energy to a part of the dermis that is in contact with the heat generator, and thus the skin may be treated.

In the present disclosure, the plurality of needles of the needle assembly may each have the same length.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
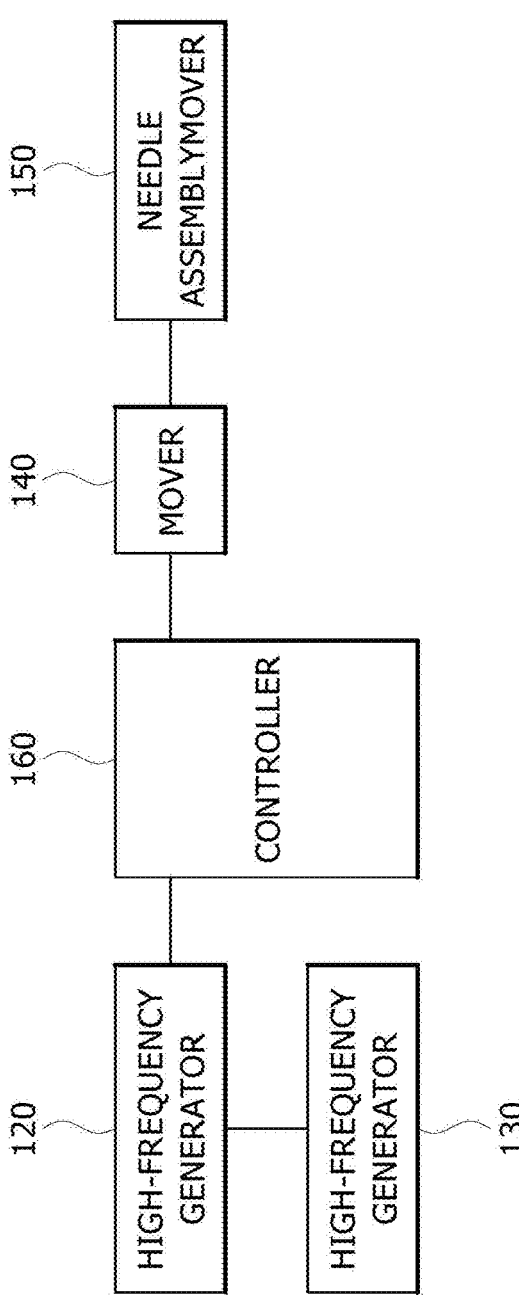
FIG. 1 is a view schematically illustrating a configuration of a high-frequency skin care device according to one embodiment of the present disclosure.

Hereinafter, a high-frequency skin care device according to one embodiment of the present disclosure will be described with reference to the accompanying drawings. In this process, thicknesses of lines or sizes of components illustrated in the drawings may be exaggerated for clarity and convenience of description.

Also, terms used herein are only used to describe specific embodiments and are not intended to limit the present disclosure. A singular expression includes a plural expression unless the context clearly indicates otherwise. In the present application, terms such as "include" or "have" are intended to designate the presence of features, numbers, steps, operations, components, parts, or combinations thereof described herein and should not be understood as precluding the possibility of presence or addition of one or more other features, numbers, steps, operations, components, parts, or combinations thereof. Terms such as "first" and "second" may be used to describe various components, but the components should not be limited by the terms. The terms are only used to distinguish one component from another component.

Hereinafter, embodiments according to the present disclosure will be described in detail with reference to the accompanying drawings, and in the description with reference to the accompanying drawings, the same or corresponding components will be denoted by the same reference numerals, and overlapping description thereof will be omitted.

Figure 2:
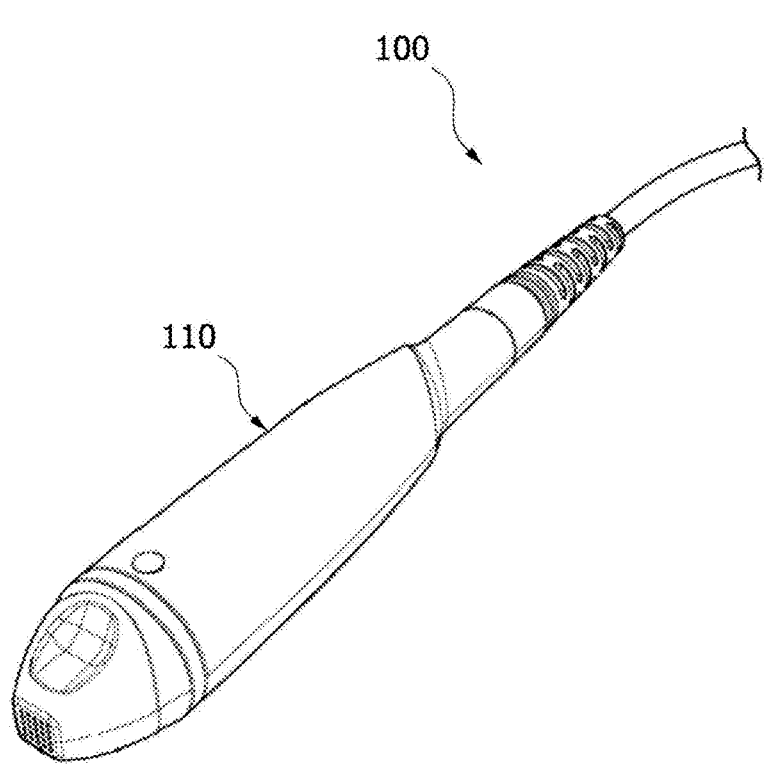
FIG. 2 is a perspective view illustrating a handpiece of the high-frequency skin care device according to one embodiment of the present disclosure.
Figure 3:
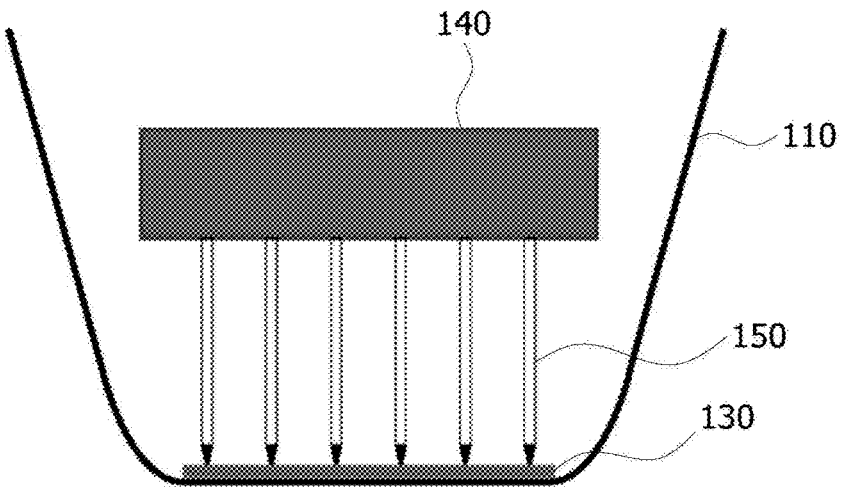
FIG. 3 is an exemplary view for describing a front end portion of the high-frequency skin care device according to the present embodiment.
Figure 4:
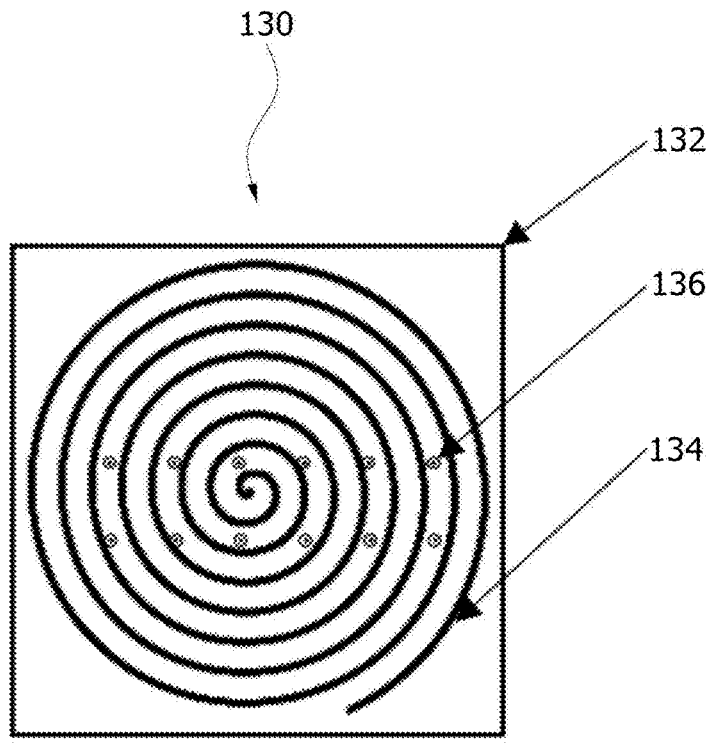
FIG. 4 is an exemplary view for describing a coil part according to one embodiment of the present disclosure.
Figure 5:
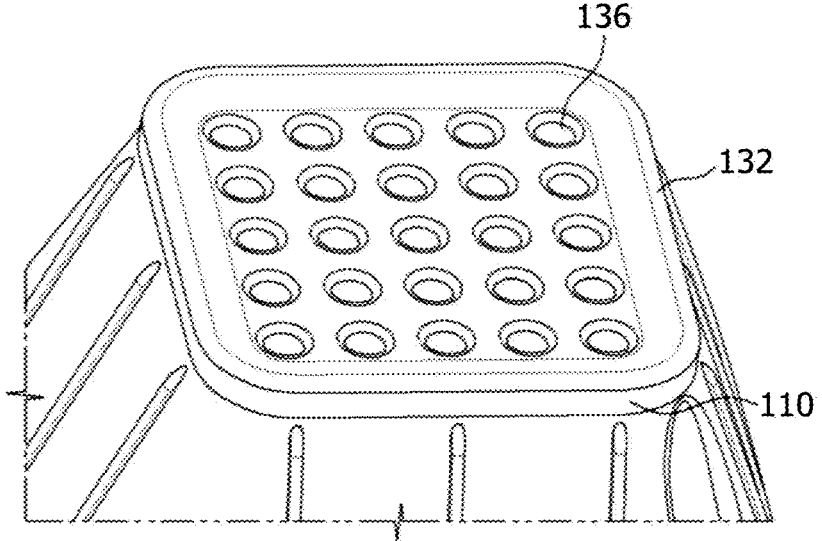
FIG. 5 is an exemplary view for describing through-holes of the coil part according to one embodiment of the present disclosure.
Figure 6:
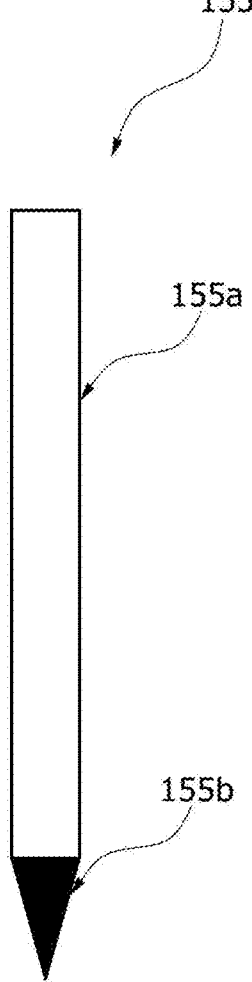
FIG. 6 is an exemplary view for describing needles according to one embodiment of the present disclosure.
Figure 7:
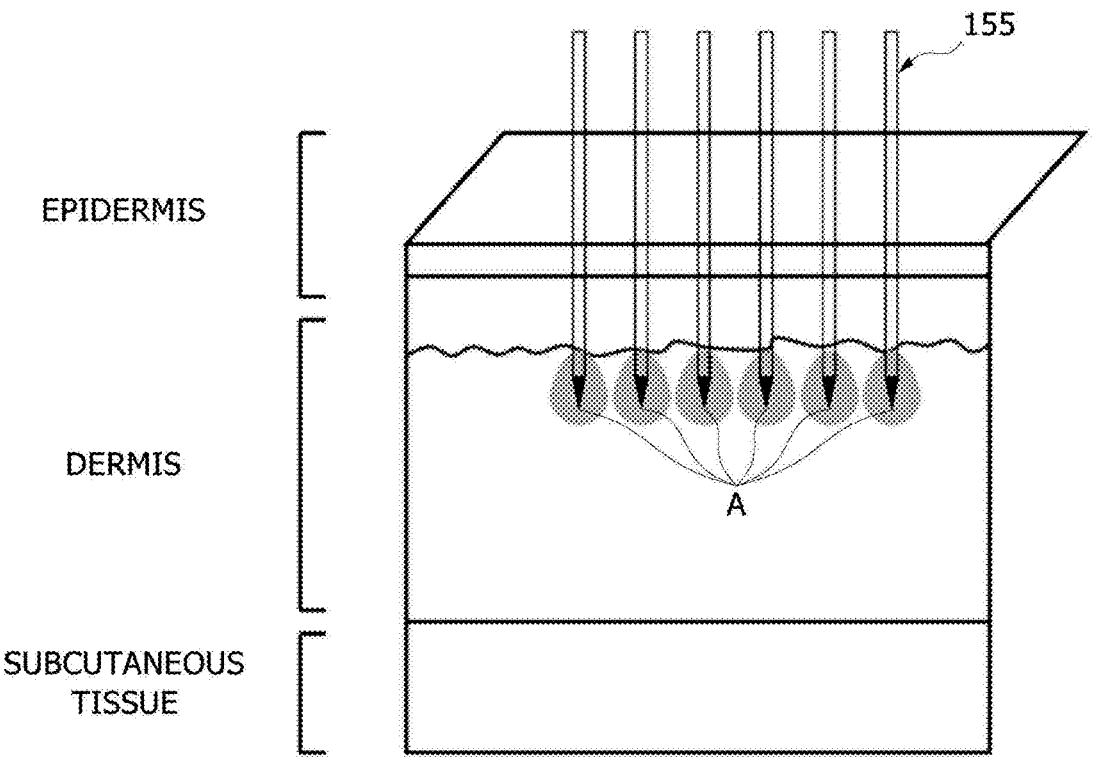
FIG. 7 is an exemplary view for describing a state in which thermal energy is output into the dermis by the needles according to one embodiment of the present disclosure.

FIG. 1 is a view schematically illustrating a configuration of a high-frequency skin care device according to one embodiment of the present disclosure, FIG. 2 is a perspective view illustrating a handpiece of the high-frequency skin care device according to one embodiment of the present disclosure, FIG. 3 is an exemplary view for describing a front end portion of the high-frequency skin care device according to the present embodiment, FIG. 4 is an exemplary view for describing a coil part according to one embodiment of the present disclosure, FIG. 5 is an exemplary view for describing through-holes of the coil part according to one embodiment of the present disclosure, FIG. 6 is an exemplary view for describing needles according to one embodiment of the present disclosure, and FIG. 7 is an exemplary view for describing a state in which thermal energy is output into the dermis by the needles according to one embodiment of the present disclosure.

Referring to FIGS. 1 and 2, a high-frequency skin care device 100 according to one embodiment of the present disclosure includes a high-frequency generator 120, a coil part 130, a mover 140, a needle assembly 150, and a controller 160. Here, the high-frequency generator 120 may be included in a main body (not illustrated) of the high-frequency skin care device, and the coil part 130, the mover 140, and the needle assembly 150 may be included in a handpiece case 110 illustrated in FIG. 2.

The handpiece case 110 also serves as a handle, which may be gripped by a user, and may have an inner space provided therein. The handpiece case 110 may have a substantially cylindrical shape and may have the inner space in which the coil part 130, the needle assembly 150, and the mover 140 are installed. The handpiece case 110 may be formed of an insulating material such as plastic.

A front end portion of the handpiece case 110 may be a portion of the handpiece case 110 that comes in contact with the skin.

The high-frequency generator 120 may receive power and output a high-frequency current.

The high-frequency generator 120 may include an inverter part (not illustrated) configured to convert direct current power to an alternating current in a range of 100 kHz to 10 MHz to generate an induced electromotive force. Specifically, the high-frequency generator 120 may include an input filter circuit (not illustrated), a primary rectifier circuit (not illustrated), a power-factor improvement circuit (not illustrated), a switching circuit (not illustrated), an isolation transformer (not illustrated), a secondary rectifier circuit (not illustrated), an inverter circuit (not illustrated), and an output common filter (not illustrated). The input filter circuit may block noise of input alternating current power, the primary rectifier circuit and the power-factor improvement circuit may set an input voltage to be in a range of 85 V to 264 V while improving the power factor, the switching circuit may switch the direct current power input from the power-factor improvement circuit and transfer the direct current power as alternating current power to the isolation transformer, the isolation transformer may control an output voltage while insulating the primary side and the secondary side, the secondary rectifier circuit may rectify the alternating current power input from the isolation transformer to direct current power, the inverter circuit may adjust a frequency to be transferred to the coil part 130, and the output common filter may remove common-mode noise included in the output power and then transmit the output power to the coil part 130.

The high-frequency generator 120 may be connected to each of a positive (+) pole and a negative (−) pole of the coil part 130 and may receive power and transmit the power to the coil part 130. The high-frequency generator 120 may cause a high-frequency current to flow in the coil part 130.

The coil part 130 may convert the high-frequency current output from the high-frequency generator 120 into an alternating magnetic field. That is, the coil part 130 may convert an alternating current input from the high-frequency generator 120 into an alternating magnetic field having energy. For example, the coil part 130 may convert an alternating current in a range of 100 kHz to 10 MHz, which is transferred from the high-frequency generator 120, into an alternating magnetic field through a coil 134.

As illustrated in FIG. 3, the coil part 130 may be disposed at the front end portion of the handpiece case 110. That is, the coil part 130 may be disposed at the portion that comes in contact with the skin.

As illustrated in FIG. 4, the coil part 130 may include the coil 134, a substrate 132 on which the coil 134 is disposed, and a plurality of through-holes 136.

The coil 134 may be disposed in a spiral shape on the substrate 132.

The coil 134 may be positioned on the substrate 132 and positioned between the substrate 132 and a close contact surface of the handpiece case 110 that comes in contact with the skin. Maximum energy transfer is possible when the coil part 130 is positioned closest to the skin.

One surface of the substrate 132 may be a close contact surface that comes in contact with the user's skin during treatment, and the other surface of the substrate 132 may have the coil 134 disposed thereon. The plurality of through-holes 136 may be formed in the substrate 132. The substrate 132 may be a concept encompassing a bobbin.

The substrate 132 may be made of a nonmetal material such as rubber, silicone, or plastic to not affect the high-frequency current flowing in the coil 134.

The plurality of through-holes 136 may be disposed on the substrate 132 and allow a plurality of needles 155 to pass therethrough between portions of the coil 134. As illustrated in FIG. 5, the plurality of through-holes 136 may be spaced apart at predetermined intervals and formed in a lattice shape. Although the plurality of through-holes 136 are formed in a lattice shape in the present embodiment, the present disclosure is not necessarily limited thereto, and the plurality of through-holes 136 may be formed in various other shapes across the front end portion of the handpiece case 110. The front end portion of the handpiece case 110 comes in contact with the user's skin.

When the needle assembly 150 is moved downward in a state in which the user's skin is pressed with the close contact surface coming in contact with the skin, the needles 155 of the needle assembly 150 move downward through the through-holes 136 and stimulate the dermis of the skin.

For the needles 155 to be easily inserted into the through-holes 136, the diameter of the through-hole 136 may be larger than the diameter of the needle 155.

By allowing the plurality of needles 155 to be positioned in the plurality of through-holes 136, the coil part 130 may prevent the plurality of needles 155 from being bent right before being inserted into the skin and may improve straightness of the plurality of needles 155.

The mover 140 may be installed in the handpiece case 110 and move the needle assembly 150 (in a vertical direction) to cause the needle assembly 150 to come in contact with or not come in contact with the skin.

The mover 140 may vertically lift or lower the plurality of needles 155. The plurality of needles 155 are fixed to the mover 140, and the plurality of needles 155 are lifted or lowered vertically due to movement of the mover 140. By the mover 140, the plurality of needles 155 may protrude from one surface of the front end portion of the handpiece case 110 and be inserted into the skin. The mover 140 may be configured to vertically move upward or downward through a separate driver (not illustrated) provided inside or outside the handpiece case 110. A motor, a ball screw, a pneumatic actuator, an electromagnetic device, or the like may be applied as the driver.

The needle assembly 150 may include the plurality of needles 155 configured to be heated by the alternating magnetic field, which is generated by the coil part 130, and come in contact with the skin to treat the skin.

The plurality of needles 155 may each be designed to be inserted into the skin at a depth of about 0.1 mm to 4 mm, current may flow in a heat generator 155b inserted into the skin due to the alternating magnetic field generated by the coil part 130, and the heat generator 155b may convert the generated current into heat due to eddy current loss and hysteresis loss which are caused by the current.

The plurality of needles 155 of the needle assembly 150 may each have the same length. The diameter of each needle 155 may be in micro units.

As illustrated in FIG. 6, the needle 155 may include a circular rod part 155a and the heat generator 155b. That is, the needle 155 may have an upper end portion configured as the circular rod part 155a which does not conduct electricity (has characteristics of a nonconductor) and has high thermal resistance and a lower end portion configured as the heat generator 155b which has conductivity and low thermal resistance.

The circular rod part 155a may be configured as an insulator (nonconductor) and have an upper end portion connected to the mover 140.

The heat generator 155b may be connected to the circular rod part 155a and generate heat due to the alternating magnetic field generated by the coil part 130.

The heat generator 155b may be configured as a conductor, current may flow in the heat generator 155b due to the alternating magnetic field, and the heat generator 155b may generate heat due to eddy current loss and hysteresis loss which are caused by the current. For example, the heat generator 155b may be made of a metal material.

The alternating magnetic field may induce an eddy current in the heat generator 155b configured as a conductor. The eddy current may be converted into heat in the heat generator 155b due to eddy current loss and hysteresis loss. The hysteresis loss may be energy loss that occurs when the heat generator 155b changes from a magnetized state to a demagnetized state due to the alternating magnetic field. The heat generated by the heat generator 155b may be transferred as thermal energy to a part of the dermis in contact with the heat generator 155b without being transferred to the circular rod part 155a with high thermal resistance. The skin may be treated by the heat transferred to the dermis of the skin.

When the needle assembly 150 is inserted into the skin, each needle 155 may be inserted into the epidermis at a depth of about 0.1 mm to 4 mm. The heat generator 155b may be inserted into the dermis of the skin and use heat to treat the skin. For example, when high-frequency waves are applied to the needle assembly 150, a plurality of thermal energy reach areas A are distributed in the thickness direction of the dermis.

The controller 160 may control the high-frequency generator 120 and the mover 140.

The controller 160 may also be connected to a switch (not illustrated) arranged on an outer side surface of the handpiece case 110. The user may operate the switch to generate a control signal.

Hereinafter, operations of the high-frequency skin care device 100 configured as above will be described.

A practitioner brings the close contact surface of the front end portion of the handpiece case 110 in close contact with the patient's skin while gripping the high-frequency skin care device 100. When the close contact surface is completely in close contact with the patient's skin, the switch (not illustrated) disposed on the handpiece case 110 may be operated to move the mover 140 downward toward the skin. When the mover 140 moves downward, the needle assembly 150 connected to the mover 140 also moves downward, and the needles 155 pass through the epidermis and prick the dermis as illustrated in FIG. 7. The moment the needles 155 are inserted into the dermis, the high-frequency generator 120 may be operated and generate high-frequency waves. The high-frequency generator 120 may transfer a high-frequency current to the coil part 130, and the coil part 130 may convert the high-frequency current output from the high-frequency generator 120 into an alternating magnetic field.

In each of the plurality of needles 155, current may flow in the heat generator 155b inserted into the skin due to the alternating magnetic field generated by the coil part 130, and the heat generator 155b may convert the current into heat due to eddy current loss and hysteresis loss which are caused by the current flowing therein. That is, the heat generator 155*b* of each needle 155 may be heated by the alternating magnetic field generated by the coil part 130 and may output thermal energy as in "A" of FIG. 7. The thermal energy output from the heat generator 155*b* of each needle 155 may coagulate tissue in the dermis and may regenerate and revitalize collagen.

As described above, in the high-frequency skin care device according to one embodiment of the present disclosure, heat is generated only at the heat generator at the tip of the needle without being generated at the circular rod part of the needle, and thus skin burns or a skin reddening phenomenon that may occur after treatment can be prevented.

Also, in the high-frequency skin care device according to one embodiment of the present disclosure, electrical energy is transferred as thermal energy into the skin using high-frequency induction heat technology, and thus skin tissue can be regenerated, and a skin care effect can be enhanced.

In a high-frequency skin care device according to one embodiment of the present disclosure, since heat is generated only at a heat generator at the tip of a needle without being generated at a circular rod part of the needle, there is an effect of preventing skin burns or a skin reddening phenomenon that may occur after treatment.

Also, in the high-frequency skin care device according to one embodiment of the present disclosure, since electrical energy is transferred as thermal energy into the skin using high-frequency induction heat technology, there is an effect of regenerating skin tissue and enhancing a skin care effect.

Meanwhile, advantageous effects of the present disclosure are not limited to the above-mentioned advantageous effects, and various other advantageous effects may be included within the scope self-evident to those of ordinary skill in the art from the content described below.

The present disclosure has been described above with reference to the embodiments illustrated in the drawings, but the description is merely illustrative, and those of ordinary skill in the art should understand that various modifications and other equivalent embodiments are possible therefrom. Therefore, the true technical protection scope of the present disclosure should be defined by the claims below.

What is claimed is:

1. An apparatus comprising:
a needle assembly in a handpiece having a front-end tip that is brought into contact with a target skin area of a patient during a skin treatment procedure,
the needle assembly, being moveable in the handpiece, comprising a plurality of skin treatment needles with an array arrangement for the skin treatment procedure, each of the plurality of skin treatment needles having dimensions for the skin treatment procedure, and having a non-conductive rod and a conductive tip at a distal end thereof; and
a substrate, at the front-end tip of the handpiece, having an outer surface with portions thereof that comes into contact with the target skin area and an inner surface having thereon a flat-shaped electromagnetic spiral element used in providing high-frequency heat induction to the conductive tips of the plurality of skin treatment needles,
the substrate having a plurality of openings, wherein each of the plurality of openings being spaced apart a first distance and disposed between a plurality of windings of the flat-shaped electromagnetic spiral element,
wherein the array arrangement of the plurality of skin treatment needles and the plurality of openings in the substrate are aligned with each other to allow the plurality of skin treatment needles to be drawn out from or drawn back into the front-end tip of the handpiece upon an activation of the needle assembly for the skin treatment procedure.

2. The apparatus of claim 1, wherein each of the plurality of windings are spaced apart a second distance.

3. The apparatus of claim 2, wherein the plurality of openings in the substrate have a lattice-like pattern with dimensions that correspond to the array arrangement of the plurality of skin treatment needles.

4. The apparatus of claim 3, wherein each of the plurality of skin treatment needles of the needle assembly is operatively attached to a heat generator element to generate heat caused by current flowing therein in relation to the high-frequency heat induction via the flat-shaped electromagnetic spiral element.

5. The apparatus of claim 4, wherein the array arrangement has rows and columns of the plurality of skin treatment needles that, with the activation of the needle assembly, are configured to cause stimulations at the target skin area during the skin treatment procedure.

6. The apparatus of claim 5, wherein each of the plurality of skin treatment needles has a same length and diameter that, with the activation of the needle assembly, are configured to cause skin penetration at a depth of approximately 0.1 mm to 4 mm to cause, via the conductive tips, tissue in a dermis under the target skin area to coagulate and to further cause regeneration or revitalization of collagen therein.

7. The apparatus of claim 6, further comprising a power source that is configured to provide a high-frequency current to the flat-shaped electromagnetic spiral element to cause heating at the conductive tips of the plurality of skin treatment needles via the high-frequency heat induction.

8. The apparatus of claim 7, wherein the power source comprises a high-frequency generator, that is separate from but operatively connected to the handpiece, and is configured to provide the high-frequency current having frequency characteristics of approximately 100 kHz to 10 MHz.

9. The apparatus of claim 8, wherein the activation of the needle assembly is performed manually, and movement of the needle assembly is achieved via a motorized mechanism in the handpiece.

10. The apparatus of claim 9, wherein the handpiece has an elongated shape that is configured to enable manual manipulation at or near the target skin area, without being attachable to the target skin area.

* * * * *